US009992855B2

United States Patent
Larroux et al.

(10) Patent No.: US 9,992,855 B2
(45) Date of Patent: Jun. 5, 2018

(54) ENERGY IMAGING WITH CONTROLLED RISE AND FALL TIMES

(71) Applicant: General Electric Company, Schenectady, NY (US)

(72) Inventors: Jean-Francois Larroux, Buc (FR); Julien Bouhraoua, Buc (FR); Aurelien Gadenne, Buc (FR)

(73) Assignee: General Electric Company, Schenectady, NY (US)

( * ) Notice: Subject to any disclaimer, the term of this patent is extended or adjusted under 35 U.S.C. 154(b) by 561 days.

(21) Appl. No.: 14/658,943

(22) Filed: Mar. 16, 2015

(65) Prior Publication Data

US 2016/0192466 A1    Jun. 30, 2016

Related U.S. Application Data

(60) Provisional application No. 62/098,009, filed on Dec. 30, 2014.

(51) Int. Cl.
*H05G 1/58* (2006.01)
*H05G 1/32* (2006.01)

(52) U.S. Cl.
CPC ............... *H05G 1/58* (2013.01); *H05G 1/32* (2013.01); *G01N 2223/419* (2013.01)

(58) Field of Classification Search
CPC .. G01N 2223/419; G01N 23/046; H05G 1/32; H05G 1/58
See application file for complete search history.

(56) References Cited

U.S. PATENT DOCUMENTS

| | | | |
|---|---|---|---|
| 4,601,051 A * | 7/1986 | Santurtun | H05G 1/54 378/105 |
| 7,813,474 B2 | 10/2010 | Wu et al. | |
| 8,031,831 B2 | 10/2011 | Zou | |
| 8,189,741 B2 | 5/2012 | Ernest et al. | |
| 8,755,491 B2 | 6/2014 | Rosevear et al. | |
| 2008/0144764 A1 * | 6/2008 | Nishide | A61B 6/4035 378/5 |

* cited by examiner

*Primary Examiner* — Glen Kao
(74) *Attorney, Agent, or Firm* — Boyle Fredrickson, S.C.

(57) ABSTRACT

Rise times and fall times provided by a high voltage generator are controlled to maintain image quality during such scans. The rise and fall times are controlled by first measuring rise and fall times at each transition. Then, a closed-loop controller is used to adjust control parameters of the high voltage generator, based on an error determined from the measurement, to achieve substantially constant rise and fall times. This invention may be based on the implementation of two closed-loop controllers on rise and fall time of fast-kV exposures. As a result, image quality may be improved and system calibration time may be reduced.

20 Claims, 3 Drawing Sheets

ENERGY IMAGING WITH CONTROLLED RISE AND FALL TIMES

CROSS-REFERENCE(S) TO RELATED APPLICATION(S)

This application claims priority to U.S. Provisional Application No. 62/098,009, filed on Dec. 30, 2014, the disclosure of which is hereby incorporated by reference in its entirety.

BACKGROUND OF THE INVENTION

The invention relates generally to imaging systems, and more particularly to high voltage generators for imaging systems.

Computed Tomography (CT) is an X-ray medical imaging process which makes possible obtaining a three-dimensional (3D) image of a patient or object using a plurality of two-dimensional (2D) images acquired about the patient or object. In CT, dual energy imaging is known for obtaining material characterizations and/or reduction of artifacts by utilizing two scans of the patient or object at different voltage/energy levels, "low-kV" and "high-kV."

In a single rotation around the patient or object, a high voltage generator switches between "low-kV" and "high-kV" in order to emit low energy X-rays and high energy X-rays, respectively, from an X-ray tube. The high voltage generator may typically switch, for example, between a low-kV of about 70 to 100 kilovolts (kV) and a high-kV of about 120 to 150 kV. The low energy and high energy X-rays emitted, after being attenuated by the patient or object, impinge upon an array of radiation detectors. The intensity of the X-rays may then be processed to produce an image.

To complete a dual energy scan in a single rotation, the high voltage generator must rapidly switch between low-kV and high-kV. Such rapid switching may typically be performed periodically at a view rate frequency range of 1 kHz to 10 kHz. However, the high voltage generator typically includes a high voltage (HV) capacitance which may include a filtering capacitor and/or parasitic capacitance (such as from high voltage cabling). As a result, the fall time between high-kV and low-kV is related to the discharge of the HV capacitance.

In CT imaging, variations of kV waveforms from one view to another may cause undesirable image quality artifacts. What is needed is an improved technique for producing kV waveforms such that variations from one view to another are minimized.

BRIEF DESCRIPTION OF THE INVENTION

In the present invention, rise times and fall times provided by a high voltage generator, such as during "dual energy" or multi-energy scans, are controlled to maintain image quality during such scans. The rise and fall times are controlled by first measuring rise and fall times at each transition. Then, a closed-loop controller is used to adjust control parameters, such as of the high voltage generator, based on an error determined from the measurement, to achieve substantially constant rise and fall times. This invention may be based on the implementation of two closed-loop controllers on rise and fall time of fast-kV exposures. As a result, image quality may be improved and system calibration time may be reduced.

By way of example, a rise time target may be 27 μs. Then, a measured rise time may be 30 μs. A closed loop controller may operate to adjust generator control parameters to meet the rise time target (27 μs) in a next waveform transition.

A conventional closed-loop proportional-integral (PI) controller architecture or proportional-integral-derivative (PID) architecture could be used. After few cycles, the system may stabilize and the rise and fall distributions may become centered on target. Accordingly, the impact of hardware variations or disturbances, such as HV (high voltage) capacitance variations, temperature changes, electrical network fluctuations, and the like, may be minimized. Improved image quality due to better fidelity of tube voltage from one exposure to another and from one system to another may be provided.

Specifically then, the present invention, in one embodiment, may provide a high voltage generator system for X-ray imaging including a high voltage generator configured to provide a first voltage and a second voltage to an X-ray tube for an energy scan. Transitions from the first voltage to the second voltage may correspond to rise times, and transitions from the second voltage to the first voltage may correspond to fall times. A first controller may be in communication with the high voltage generator in a first control loop. The first controller may be configured to adjust the high voltage generator according to: (a) a target voltage; and (b) feedback indicating a voltage level from the high voltage generator. A second controller may be in communication with the first control loop. The second controller may be configured to adjust a parameter of the first control loop according to: (a) at least one of a target rise time and a target fall time; and (b) feedback indicating at least one of a rise time and a fall time from the high voltage generator.

Also, a method for providing a first voltage and a second voltage to an X-ray tube for an energy scan, in which transitions from the first voltage to the second voltage correspond to rise times and transitions from the second voltage to the first voltage correspond to fall times, may include: adjusting a high voltage generator in a first control loop according to: (a) a target voltage; and (b) feedback indicating a voltage level from the high voltage generator; and adjusting a parameter of the first control loop according to: (a) at least one of a target rise time and a target fall time; and (b) feedback indicating at least one of a rise time and a fall time from the high voltage generator.

Also, a CT imaging system may include a gantry; an X-ray tube disposed on the gantry; and a high voltage generator system including: (a) a high voltage generator configured to provide a first voltage and a second voltage to the X-ray tube for an energy scan, in which transitions from the first voltage to the second voltage correspond to rise times and transitions from the second voltage to the first voltage correspond to fall times; (b) a first controller in communication with the high voltage generator in a first control loop, the first controller configured to adjust the high voltage generator according to: (1) a target voltage; and (2) feedback indicating a voltage level from the high voltage generator; and (c) a second controller in communication with the first control loop, the second controller configured to adjust a parameter of the first control loop according to: (1) at least one of a target rise time and a target fall time; and (2) feedback indicating at least one of a rise time and a fall time from the high voltage generator.

DETAILED DESCRIPTION OF THE INVENTION

Figure 1:
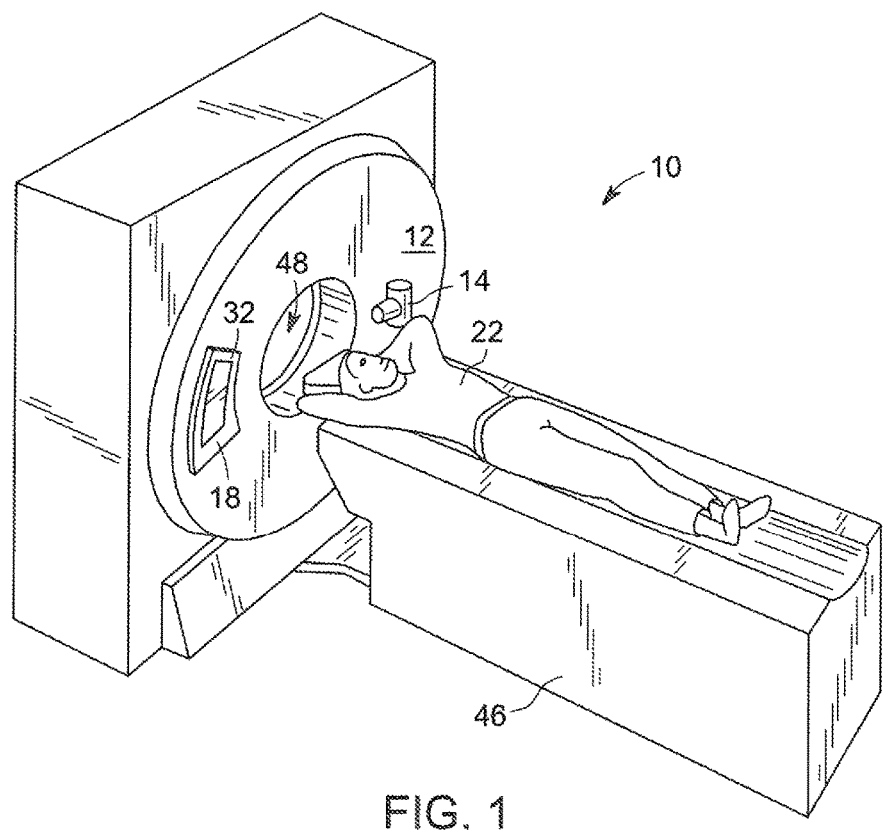
FIG. 1 is a pictorial view of an exemplar CT imaging system in accordance with an embodiment of the invention.
Figure 2:
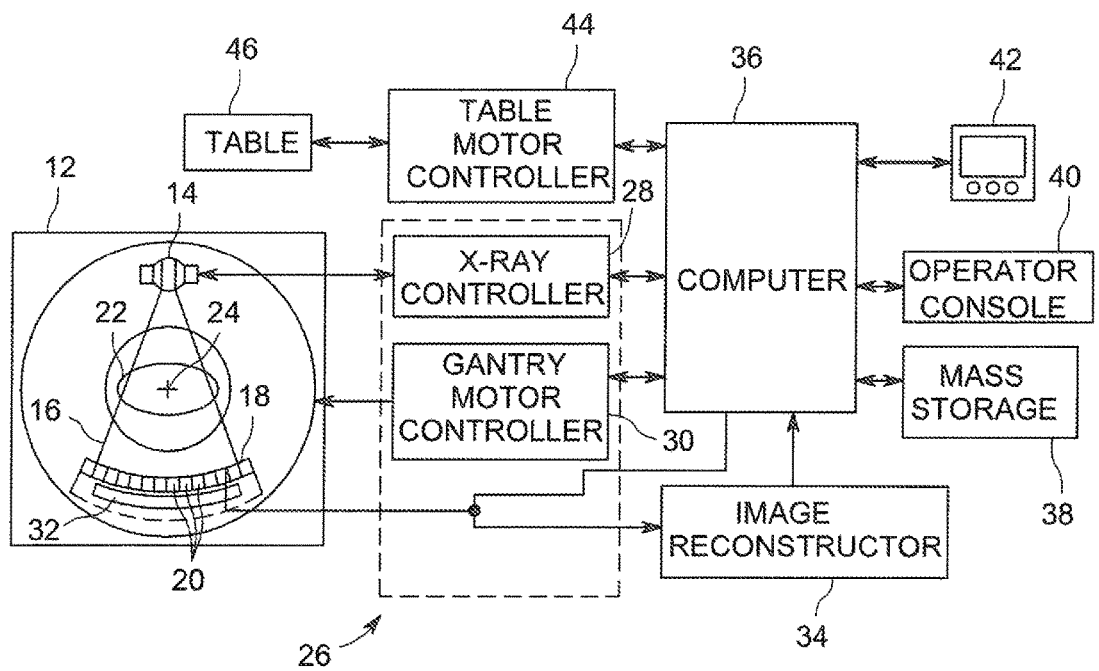
FIG. 2 is a block schematic diagram of the system illustrated in FIG. 1.

Referring now to FIG. 1, an exemplary computed tomography (CT) imagining system 10 is shown as including a gantry 12 which may be representative of a "third generation" CT scanner. The gantry 12 includes an X-ray source 14 which projects a polychromatic beam of X-rays 16 toward a detector assembly 18 on an opposite side of the gantry 12. Typically, a collimator may be an integral part of the detector assembly 18. Referring also to FIG. 2, the detector assembly 18 may be formed by a plurality of detectors 20 and data acquisition systems (DAS) 32. The plurality of detectors 20 sense the projected X-rays which pass through a patient 22 or object, and the DAS 32 converts corresponding data to digital signals for subsequent processing. Each detector 20 produces an analog electrical signal that represents the intensity of an impinging X-ray beam, and hence the attenuated beam as it passes through the patient 22. During a scan to acquire X-ray projection data, the gantry 12 and the components mounted thereon rotate about a center of rotation 24.

Rotation of the gantry 12 and the operation of X-ray source 14 are governed by a control mechanism 26 of CT system 10. The control mechanism 26 includes a high voltage generator system 28 that provides power and timing signals to an X-ray source 14 (X-ray tube) and a gantry motor controller 30 that controls the rotational speed and position of the gantry 12. An image re-constructor 34 receives sampled and digitized X-ray data from the DAS 32 and performs high speed reconstruction. The reconstructed image is applied as an input to a computer 36 which stores the image in a mass storage device 38.

The computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by the computer 36 to provide control signals and information to the DAS 32, the high voltage generator system 28 and the gantry motor controller 30. In addition, the computer 36 operates a table motor controller 44 which controls a motorized table 46 to position the patient 22 and the gantry 12. In particular, the motorized table 46 is operable to move the patient 22 through a gantry opening 48, as illustrated in FIG. 1, in whole or in part.

Figure 3:
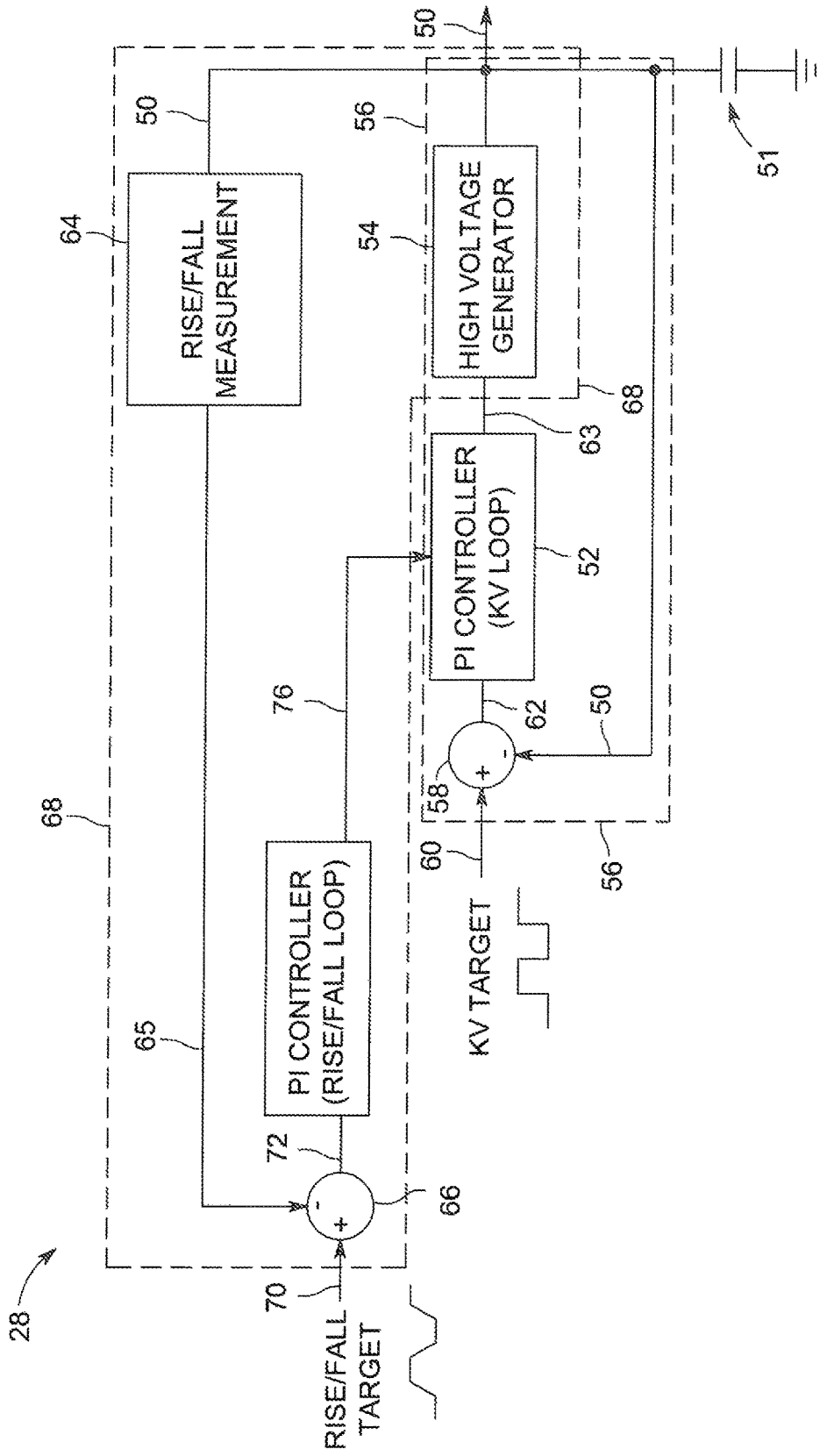
FIG. 3 is a simplified diagram of an architecture for a high voltage generator controller for the system of FIGS. 1 and 2.

Referring now to FIG. 3, by way of example, the high voltage generator system 28 may be configured to provide a voltage level 50 corresponding to a first voltage/energy level (low-kV or "low voltage") at certain times and a second voltage/energy level (high-kV "high voltage") at other times to the X-ray source 14 for a dual energy scan. The first voltage/energy level (low-kV) may be about 70 to 100 kilovolts (kV), and the second voltage/energy level (high-kV) may be about 120 to 150 kV, for example. To complete a dual energy, the high voltage generator system 28 may switch periodically, between the low voltage and the high voltage, at a view rate frequency range of 500 Hz to 10 kHz. Accordingly, the voltage level 50 provides a waveform in having a duty cycle and period which cycles between the low voltage and the high voltage. Transitions from the low voltage to the high voltage correspond to "rise times," and transitions from the high voltage to the low voltage correspond to "fall times."

The voltage level 50 is also typically subject to a high voltage (HV) capacitance 51. The HV capacitance 51 may represent a filtering capacitor and/or parasitic capacitance (such as from high voltage cabling) of the X-ray generator system 28. As a result, the rise times and fall times of the voltage level 50 may be variable, thereby necessitating correction according to the present invention.

Accordingly, a first controller 52 is in communication with a high voltage generator 54 in a first control loop 56. The first controller 52 is configured to control and adjust the high voltage generator 54 to produce the voltage level 50 (corresponding to the low voltage at certain times and the high voltage at other times according to the period of the dual energy scan). The high voltage generator 54 may include one or more "chopping" and/or rectification stages with associated frequencies for producing the voltage level 50.

In the first control loop 56, the voltage level 50 is fed back to a first comparator 58. The first comparator 58, in turn, compares the voltage level 50 to an idealized target voltage 60 (corresponding to the low voltage at certain times and the high voltage at other times according to the period of the dual energy scan). The first comparator 58 then provides a first compared signal 62 (representing a measured voltage level error) to the first controller 52 for adjusting the high voltage generator 54, via a first control signal 63, to more closely meet the target voltage 60.

The first controller 52 may be a proportional-integral (PI) controller having a proportional gain and an integral gain. Alternatively, the first controller 52 could be proportional-integral-derivative (PID) controller having a proportional gain, an integral gain and a derivative gain or other controller as known in the art. The first controller 52 may calculate an error value as the difference between the voltage level 50 (measured process variable) and the target voltage 60 (desired set point). The first controller 52 may attempt to minimize the error by adjusting the high voltage generator 54 via the first control signal 63.

In addition, the voltage level 50 is measured with respect to rise times and fall times, such as via a timing circuit 64. Measured rise times and fall times 65 are fed back to a second comparator 66 in a second control loop 68. The second comparator 66, in turn, compares the measured rise times and fall times 65 of the voltage level 50 to target rise times and fall times 70. The target rise times and fall times 70 may be selected for achieving substantially constant rise times and fall times for each cycle during the dual energy scan. The second comparator 66 then provides a second compared signal 72 (representing a measured rise/fall time error) to a second controller 74 for adjusting a parameter of the first control loop 56 via a second control signal 76 to the first controller 52.

The second controller 74 may also be a proportional-integral (PI) controller having a proportional gain and an integral gain. Alternatively, the second controller 74 could also be proportional-integral-derivative (PID) controller having a proportional gain, an integral gain and a derivative gain or other controller as known in the art. The second controller 74 may calculate an error value as the difference between the measured rise times and fall times of the voltage level 50 (measured process variable) and the target rise times and fall times 70 (desired set point). The second controller 74 may attempt to minimize the error by adjusting the first controller 52, via the second control signal 76.

In one instance, the second controller 74 may adjust a gain of the first controller 52. The second controller 74 may adjust the gain of the first controller 52 according to a target rise time.

In another instance, the second controller 74 may adjust a frequency or duty cycle of the high voltage generator 54. The second controller 74 may adjust a frequency or duty cycle of the high voltage generator 54 according to a target fall time.

Figure 4:
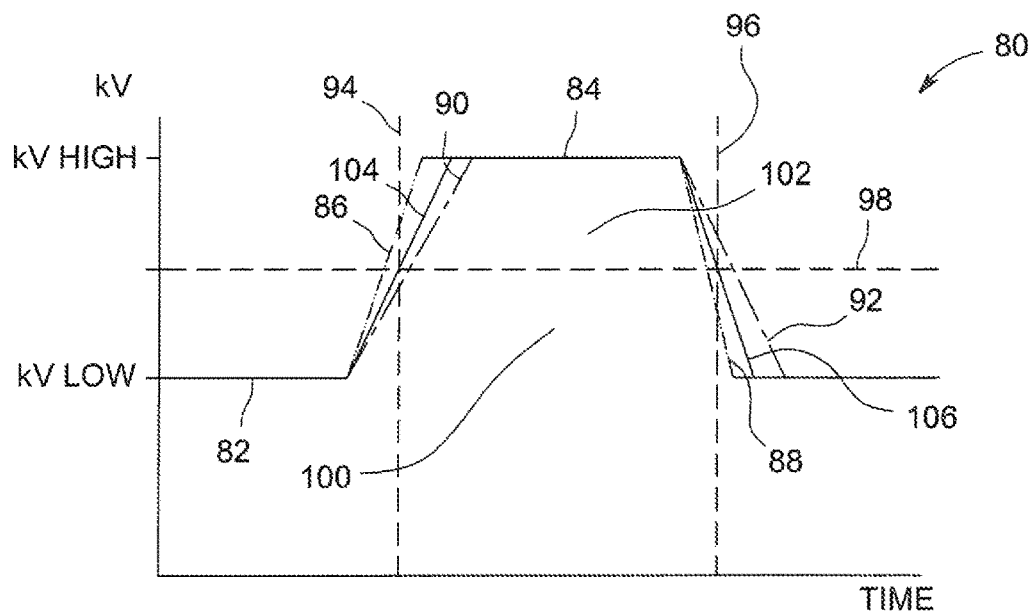
FIG. 4 is a graph illustrating a high voltage waveform in an exemplary dual energy scan.

Referring now to FIG. 4, a graph illustrating a waveform 80 which may be produced by the controlled high voltage generator system of FIG. 3 is shown. The high voltage generator system 28 may provide the voltage level 50 corresponding to a low voltage 82 at certain times and a high voltage 84 at other times, according to a period, for a dual energy scan. To complete the dual energy, the high voltage generator system 28 switches from cycle to cycle, between the low voltage and the high voltage, at a view rate frequency range of 500 Hz to 10 kHz.

Without the first and second control loops 56 and 68, respectively, enabled, the high voltage generator system 28 produces fast rise times 86 and fast fall times 88 at certain times, and slow rise times 90 and slow fall times 92 at other times. This variation may occur, for example, due to charging and discharging the HV capacitance 51 at varying rates and times. Rise times and fall times may be measured with respect to 10% and 90% of the transition.

As illustrated by a separation midpoint 98, an undesirable disproportionate energy separation may occur due to the aforementioned fast and slow variations of the rise and fall times. In particular, energy amounts transferred during low voltage times 100 (below the separation midpoint 98) may vary significantly from energy amounts transferred during high voltage times 102 (above the separation midpoint 98).

Accordingly, the high voltage generator system 28 is operable to produce a controlled rise time 104 and a controlled fall time 106. For example, according to the dual energy scan frequency rate and amount of the HV capacitance 51, a target rise time (ultimately corresponding to the controlled rise time 104) and a target fall time (ultimately corresponding to the controlled fall time 106) may be determined. A target rise time and a target fall time each may be, for example, 27 μs.

Then, actual rise times and a fall times from the high voltage generator 28 may be measured and in the second control loop 68. For example, the slow rise time 90 and the slow tall time 92 each may be measured, for example, at 30 μs. The second controller 74 may attempt to minimize the error (3 μs) by adjusting the first controller 52, via the second control signal 76. The high voltage generator 28 may then meet the target rise time and a target fall time in subsequent transitions. The system may stabilize with the rise and fall distributions centered on the controlled rise time 104 and the controlled fall time 106. Accordingly, the technical effect is that hardware variations or disturbances, such as HV (high voltage) capacitance variations, temperature changes, electrical network fluctuations, and the like, may be minimized.

Figure 5:
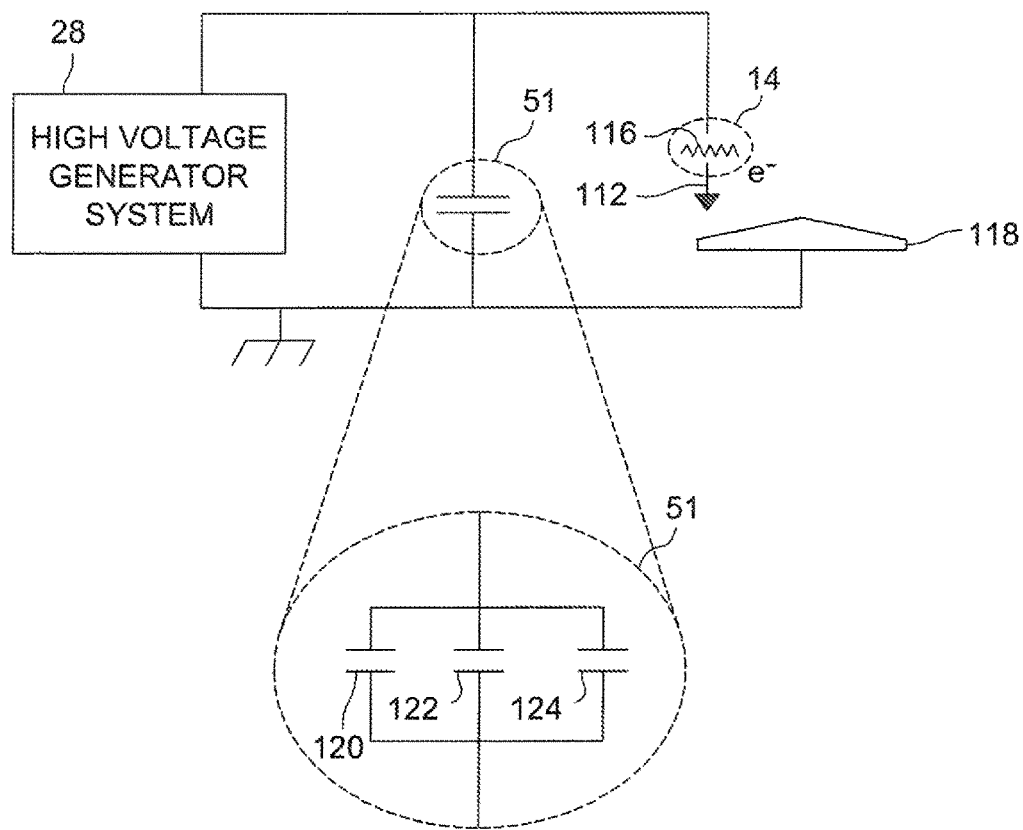
FIG. 5 is a simplified schematic of the X-ray generator system and X-ray source of FIGS. 1-4.

Referring now to FIG. 5, a simplified schematic of the X-ray generator system and X-ray source of FIGS. 1-4 is provided. For a dual energy scan, the high voltage generator system 28 controls the high voltage generator 54 to switch between the low voltage 82 and the high voltage 84 with respect to the X-ray source 14 in order to emit low energy and high energy X-rays, respectively, via the X-ray source 14. In particular, the high voltage generator system 28 may control energy of electrons 112 that are emitted by a filament 116 (such as a heating filament) of the X-ray source 14 toward an anode 118 of the X-ray source 14.

To adjust the X-ray exposure, such as for different parts of the body or differently sized objects, the X-ray source 14 may be controlled by the high voltage generator system 28, for example, to provide tube current modulation. The X-ray source 14 provides the tube current (at a voltage/energy level in accordance with the high voltage generator system 28). In particular, the filament 116 may release the electrons 112 in varying amounts, based on varying control of the filament 116, toward the anode 118

The high voltage (HV) capacitance 51 may include a high voltage generator capacitance 120 (resulting from the high voltage generator 54), a high voltage cable capacitance 122, and/or a high voltage tube capacitance 124 (resulting from the X-ray source 14). Additional filtering capacitance for filtering the low-kV and high-kV may also be included.

Alternative aspects of the invention may include providing energy scans with more than two energy levels. For example, one or more closed-loop controllers could be used to adjust control parameters of the high voltage generator to achieve substantially constant rise and fall times from a third energy level (high-kV') to a second energy level (high-kV), from a fourth energy level (high-kV") to the third energy level (high-kV'), and so forth. Such control may allow substantially constant rise and fall times between the respective energy levels. These alternative aspects are within the scope of the present inventions.

The written description uses examples to disclose the invention, including the best mode, and also to enable any person skilled in the art to practice the invention, including making and using any de ices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A high voltage generator system for X-ray imaging, comprising:
   a high voltage generator configured to provide a first voltage and a second voltage to an X-ray tube for an energy scan, wherein transitions from the first voltage to the second voltage correspond to rise times and transitions from the second voltage to the first voltage correspond to fall times;
   a first controller in communication with the high voltage generator in a first control loop, the first controller configured to adjust the high voltage generator according to:
   (a) a target voltage; and
   (b) feedback indicating a voltage level from the high voltage generator; and
   a second controller in communication with the first control loop, the second controller configured to adjust a parameter of the first control loop according to:
   (a) at least one of a target rise time and a target fall time; and (b) feedback from the high voltage generator indicating at least one of a rise time for comparing to the target rise time and a fall time for comparing to the target fall time.

2. The high voltage generator system of claim 1, wherein the first and second controllers are either proportional-integral (PI) or proportional-integral-derivative (PID) controllers.

3. The high voltage generator system of claim 1, wherein the parameter corresponds to a gain of the first controller.

4. The high voltage generator system of claim 3, wherein the second controller adjusts the gain according to a target rise time.

5. The high voltage generator system of claim 3, wherein the second controller adjusts the gain according to a target fall time.

6. The high voltage generator system of claim 1, wherein the parameter corresponds to a frequency or duty cycle of the high voltage generator.

7. The high voltage generator system of claim 6, wherein the second controller adjusts the frequency or duty cycle according to a target rise time.

8. The high voltage generator system of claim 6, wherein the second controller adjusts the frequency or duty cycle according to a target fall time.

9. The high voltage generator system of claim 1, further comprising a timing circuit for measuring at least one of a rise time and a fall time, wherein the feedback indicating at least one of a rise time and a fall time is provided via the timing circuit.

10. A method for providing a first voltage and a second voltage to an X-ray tube for an energy scan, wherein transitions from the first voltage to the second voltage correspond to rise times and transitions from the second voltage to the first voltage correspond to fall times, the method comprising:
adjusting a high voltage generator in a first control loop according to:
(a) a target voltage; and
(b) feedback indicating a voltage level from the high voltage generator; and
adjusting a parameter of the first control loop according to:
(a) at least one of a target rise time and a target fall time; and
(b) feedback from the high voltage generator indicating at least one of a rise time for comparing to the target rise time and a fall time for comparing to the target fall time.

11. The method of claim 10, further comprising using either a proportional-integral (PI) or a proportional-integral-derivative (PID) controller to adjust the high voltage generator in the first control loop.

12. The method of claim 11, wherein the parameter corresponds to a gain of the PI controller.

13. The method of claim 10, further comprising using either a proportional-integral (PI) or proportional-integral-derivative (PID) controller to adjust the parameter of the first control loop.

14. The method of claim 13, wherein the parameter corresponds to a frequency or duty cycle of the high voltage generator.

15. The method of claim 10, further comprising using a timing circuit measuring at least one of a rise time and a fall time to provide the feedback indicating at least one of a rise time and a fall time for adjusting the parameter of the first control loop.

16. A CT imaging system comprising:
a gantry;
an X-ray tube disposed on the gantry; and
a high voltage generator system including:
(a) a high voltage generator configured to provide a first voltage and a second voltage to the X-ray tube for an energy scan, wherein transitions from the first voltage to the second voltage correspond to rise times and transitions from the second voltage to the first voltage correspond to fall times;
(b) a first controller in communication with the high voltage generator in a first control loop, the first controller configured to adjust the high voltage generator according to:
(1) a target voltage; and
(2) feedback indicating a voltage level from the high voltage generator; and
(c) a second controller in communication with the first control loop, the second controller configured to adjust a parameter of the first control loop according to:
(1) at least one of a target rise time and a target fall time; and
(2) feedback from the high voltage generator indicating at least one of a rise time for comparing to the target rise time and a fall time for comparing to the target fall time.

17. The CT imaging system of claim 16, wherein the first and second controllers are either proportional-integral (PI) or proportional-integral-derivative (PID) controllers.

18. The CT imaging system of claim 16, wherein the parameter corresponds to a gain of the first controller.

19. The CT imaging system of claim 16, wherein the parameter corresponds to a frequency or duty cycle of the high voltage generator.

20. The CT imaging system of claim 16, further comprising a timing circuit for measuring at least one of a rise time and a fall time, wherein the feedback indicating at least one of a rise time and a fall time is provided via the timing circuit.

* * * * *